US011978325B2

(12) United States Patent
Goodman et al.

(10) Patent No.: US 11,978,325 B2
(45) Date of Patent: *May 7, 2024

(54) DRUG PRODUCT PACKAGING SYSTEM INCLUDING LOCKING SYSTEM FOR CONTROLLING ACCESS TO DRUG PRODUCT CELLS

(71) Applicant: PARATA SYSTEMS, LLC, Durham, NC (US)

(72) Inventors: Mark Luke Goodman, Durham, NC (US); Sam Thomas Beeler, Durham, NC (US)

(73) Assignee: PARATA SYSTEMS, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/182,677

(22) Filed: Mar. 13, 2023

(65) Prior Publication Data

US 2023/0215236 A1 Jul. 6, 2023

Related U.S. Application Data

(63) Continuation of application No. 17/212,301, filed on Mar. 25, 2021, now Pat. No. 11,605,259.

(Continued)

(51) Int. Cl.
*G07F 5/26* (2006.01)
*G07F 11/62* (2006.01)
(Continued)

(52) U.S. Cl.
CPC ............... *G07F 5/26* (2013.01); *G07F 11/62* (2013.01); *G07F 17/0092* (2013.01); *G16H 20/13* (2018.01)

(58) Field of Classification Search
CPC ........ G07F 5/26; G07F 11/62; G07F 17/0092; G16H 20/13
See application file for complete search history.

(56) References Cited

U.S. PATENT DOCUMENTS

| 5,392,951 A | 2/1995 | Gardner et al. |
| 5,940,306 A | 8/1999 | Gardner et al. |

(Continued)

FOREIGN PATENT DOCUMENTS

| KR | 20000038312 A | 7/2000 |
| WO | 2012121365 A1 | 9/2012 |

OTHER PUBLICATIONS

International Search Report and Written Opinion corresponding to PCT/US2021/024109; dated Jul. 14, 2021 (11 pages).

(Continued)

*Primary Examiner* — Michael Collins
(74) *Attorney, Agent, or Firm* — Myers Bigel, P.A.

(57) ABSTRACT

A system includes a drug product packaging system that is configured to hold a plurality of cells in a lockable section thereof and to maintain the plurality of cells in a locked state via a locking mechanism, the locking mechanism being configured to receive ones of the plurality of cells into the lockable section of the drug product packaging system and configured to maintain the ones of the plurality of cells in the locked state without changing the locked state of previously received ones of the plurality of cells into the lockable section of the drug product packaging system.

20 Claims, 15 Drawing Sheets

Related U.S. Application Data

(60) Provisional application No. 62/994,497, filed on Mar. 25, 2020.

(51) Int. Cl.
*G07F 17/00* (2006.01)
*G16H 20/13* (2018.01)

(56) References Cited

U.S. PATENT DOCUMENTS

| | | | |
|---|---|---|---|
| 6,039,467 A * | 3/2000 | Holmes | G16H 20/13 |
| | | | 700/231 |
| 6,640,159 B2 * | 10/2003 | Holmes | A47B 88/994 |
| | | | 700/242 |
| 7,142,944 B2 | 11/2006 | Holmes et al. | |
| 8,517,215 B2 | 8/2013 | Shafir | |
| 9,532,666 B2 | 1/2017 | Savage et al. | |
| 11,605,259 B2 * | 3/2023 | Goodman | G07F 17/0092 |
| 2001/0032035 A1 * | 10/2001 | Holmes | A47B 88/994 |
| | | | 700/231 |
| 2005/0040931 A1 | 2/2005 | Shitan | |
| 2006/0049200 A1 | 3/2006 | Savage et al. | |
| 2010/0200448 A1 | 8/2010 | Doi | |
| 2010/0290877 A1 | 11/2010 | Landau et al. | |
| 2012/0095593 A1 | 4/2012 | Clarke et al. | |
| 2014/0097195 A1 | 4/2014 | Anthony et al. | |
| 2016/0062271 A1 | 3/2016 | Leemhuis et al. | |
| 2016/0331640 A1 | 11/2016 | Koike et al. | |
| 2021/0093513 A1 | 4/2021 | Nishio et al. | |
| 2021/0166799 A1 | 6/2021 | Yuyama | |

OTHER PUBLICATIONS

International Search Report and Written Opinion corresponding to PCT/US2021/024109; dated Jul. 14, 2021 (12 pages).

* cited by examiner

| | Drug Product Name | Drug Product Code | Cell Capacity | Cell Address |
|---|---|---|---|---|
| Lock/Unlock | Drug A | A234-23987 | 6000 | F4 |
| N/A | Drug B | B2343 20GH | 12000 | A3 |
| N/A | Drug C | C2342-TY | 6000 | D5 |
| N/A | Drug D | D-23423 | 5000 | C9 |
| N/A | Drug E | E3454 317 | 12000 | A6 |
| Lock/Unlock | Drug F | F2386-84 | 9000 | F8 |
| N/A | Drug G | G686J YJ | 12000 | B2 |
| Lock/Unlock | Drug H | H5656 7-LKH | 12000 | F1 |
| N/A | Drug I | I-34534 | 6000 | E3 |

*FIG. 4*

DRUG PRODUCT PACKAGING SYSTEM INCLUDING LOCKING SYSTEM FOR CONTROLLING ACCESS TO DRUG PRODUCT CELLS

CROSS-REFERENCE TO RELATED APPLICATION

The present application is a continuation of U.S. application Ser. No. 17/212,301, filed Mar. 25, 2021, which claims priority to U.S. Provisional Patent Application No. 62/994,497, filed Mar. 25, 2020, the disclosures of which are hereby incorporated herein by reference in their entireties.

BACKGROUND

The present disclosure relates generally to the dispensing of drug products, and, in particular, to securing cells containing restricted access drug products in drug product packaging systems.

Drug product packaging systems may be used in facilities, such as pharmacies, including central fill or mail order pharmacies, hospitals, long term care facilities, and the like to dispense medications to fill prescriptions. These drug product packaging systems may include systems designed to package medications in various container types including, but not limited to, pouches, vials, bottles, blistercards, and strip packaging. A drug product packaging system may include multiple cells for storing drug products for dispensing and packaging into an order for a customer or patient. Some drug products, however, have restrictive laws and/or regulations that govern the management of these drug products in a facility. For example, controlled substances, opiates, narcotics, and the like may be required to be stored in a safe or other access-controlled storage unit when not being used. Thus, cells containing restricted access drug products may need to be removed from a drug product packaging system during non-business hours and stored in an access controlled, e.g., lockable, storage unit. It may also be desirable to limit access to cells containing high cost drugs and/or any drug that may be a potential target for theft. Some drug product packaging systems may contain a lockable section for certain cells allowing restricted access drug products to remain in these cells in the drug product packaging system during non-business hours. The locking mechanism on these drug product packaging systems, however, typically includes a bar across the opening for inserting or removing the cells thereby requiring the locking mechanism to be unlocked before insertion of a cell.

SUMMARY

In some embodiments of the inventive concept, a system comprises: a drug product packaging system that is configured to hold a plurality of cells in a lockable section thereof and to maintain the plurality of cells in a locked state via a locking mechanism, the locking mechanism being configured to receive ones of the plurality of cells into the lockable section of the drug product packaging system and configured to maintain the ones of the plurality of cells in the locked state without changing the locked state of previously received ones of the plurality of cells into the lockable section of the drug product packaging system.

In other embodiments, the locking system comprises a plurality of latches, each of the plurality of latches being configured to receive a respective one of the plurality of cells, each of the plurality of latches being configurable between a lock position to maintain the respective one of the plurality of cells in the locked state and an unlock position to maintain the respective one of the plurality of cells in an unlocked state.

In still other embodiments, each of the plurality of latches comprises: a sloped receiving portion; a wall coupled to the sloped receiving portion at a junction; and a tab coupled to the wall.

In still other embodiments, the wall of each respective one of the plurality of latches is configured to block removal of the respective one of the plurality of cells when the respective one of the plurality of latches is in the lock position; and the wall of each respective one of the plurality of latches is configured to facilitate removal of the respective one of the plurality of cells when the respective one of the plurality of latches is in the unlock position.

In still other embodiments, the locking system further comprises: a plurality of springs respectively associated with the plurality of latches, respective ones of the plurality of springs being in a compressed state when respective ones of the plurality of latches are in the unlock position and being in an extended state when respective ones of the plurality of latches are in the lock position.

In still other embodiments, the plurality of springs are configured to engage the sloped receiving portions of the plurality of latches, respectively.

In still other embodiments, each of the plurality of springs is a torsion-type spring or a compression-type spring.

In still other embodiments, the locking system further comprises: a rod comprising a plurality of members extending therefrom, the plurality of members corresponding to the plurality of latches, respectively; and an actuator that is coupled to the rod and is configured to rotate the rod between a first position in which the plurality of members of the rod engage the plurality of tabs of the plurality of latches to configure the plurality of latches in the unlock position and to configure the plurality of springs in the compressed state and a second position to configure the plurality of latches in the lock position and the plurality of springs in the extended state.

In still other embodiments, the system further comprises a controller that is configured to generate a control signal in a lock state or an unlock state. The actuator is configured to rotate the rod to the first position responsive to the control signal being generated in the unlock state and is configured to rotate the rod to the second position responsive to the control signal being generated in the lock state.

In still other embodiments, the controller is configured to generate the control signal in the lock state when the rod has been in the first position for a time threshold.

In still other embodiments, the time threshold is about two minutes.

In still other embodiments, the controller is configured to generate the control signal responsive to user input.

In still other embodiments, the controller is configured to record an identification of a user that provides the user input.

In still other embodiments, the actuator is a piston type actuator.

In still other embodiments, the system further comprises a latch that is configured to hold the rod in the first position in which the plurality of members engage the plurality of tabs of the plurality of latches to configure the plurality of latches in the unlock position and to configure the plurality of springs in the compressed state.

In some embodiments of the inventive concept, a method comprises: receiving, using a locking mechanism, a first cell into a lockable section of a drug product packaging system;

maintaining, using the locking mechanism, the first cell in a locked state; and receiving, using the locking mechanism, a second cell into the lockable section of the drug product packaging system without changing the locked state of the first cell.

In further embodiments, the method further comprises: generating a control signal in a lock state or an unlock state; operating the locking mechanism to unlock the lockable section of the drug product packaging system responsive to the control signal being in the unlock state such that the first cell and the second cell are maintained in an unlocked state; and operating the locking mechanism to lock the lockable section of the drug product packaging system responsive to the control signal being in the lock state such that the first cell and the second cell are maintained in the locked state.

In still further embodiments, the method further comprises: generating the control signal in the lock state when the lockable section of the drug product packaging system has been unlocked for a time threshold.

In still further embodiments, generating the control signal comprises generating the control signal responsive to user input.

In still further embodiments, the method further comprises recording an identification of a user that provides the user input.

Other apparatus, systems, methods, articles of manufacture, and/or computer program products according to embodiments of the inventive concept will be or may become apparent to one with skill in the art upon review of the following drawings and detailed description. It is intended that all such additional apparatus, systems, methods, articles of manufacture, and/or computer program products be included within this description, be within the scope of the present inventive subject matter, and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which:

FIG. 4 is a diagram of a user interface for controlling access to drug product cells in a drug product packaging system in accordance with some embodiments of the inventive concept;

DETAILED DESCRIPTION

Figure 1:
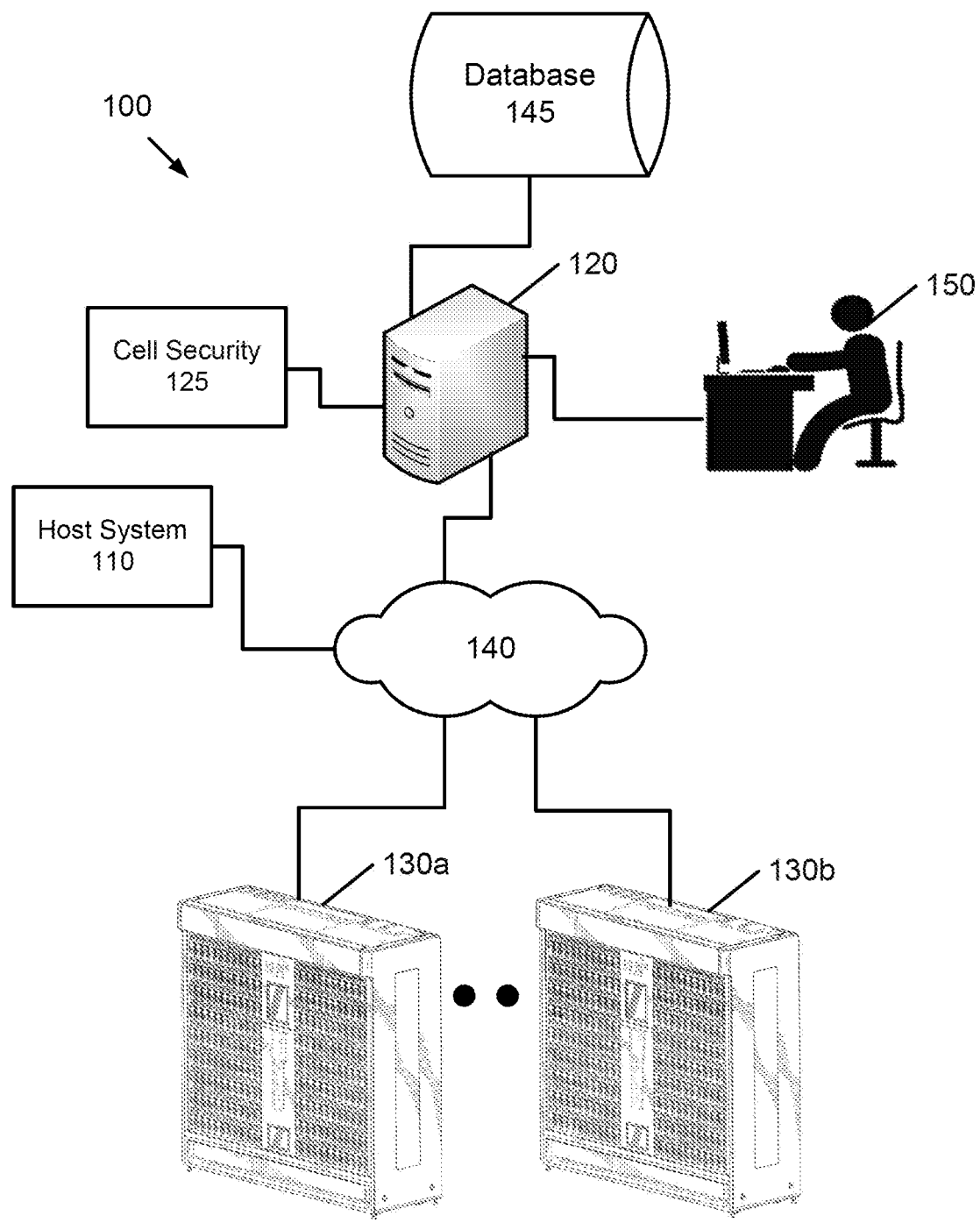
FIG. 1 is a block diagram that illustrates a communication network including a packaging system management server for controlling access to drug product cells in a drug product packaging system in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components, and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "data processing facility" includes, but it is not limited to, a hardware element, firmware component, and/or software component. A data processing system may be configured with one or more data processing facilities.

The term "drug product packaging system," as used herein, refers to any type of pharmaceutical dispensing system including, but not limited to, automated systems that fill vials, bottles, containers, pouches, blistercards, or the like with drug product, semi-automated systems that fill vials, bottles, containers, pouches, blistercards, or the like with drug product, and any combination of automated and semi-automated systems for filling a drug product package with drug product. "Drug product packaging system" also includes packaging systems for pharmaceutical alternatives, such as nutraceuticals and/or bioceuticals.

The terms "pharmaceutical" and "medication," as used herein, are interchangeable and refer to medicaments prescribed to patients either human or animal. A pharmaceutical or medication may be embodied in a variety of ways including, but not limited to, pill form capsule form, tablet form, and the like.

The term "drug product" refers to any type of medicament that can be packaged within a vial, bottle, container, pouch, blistercard, or the like by automated and semi-automated drug product packaging systems including, but not limited to, pills, capsules, tablets, caplets, gel caps, lozenges, and the like. Drug product also refers to pharmaceutical alternatives, such as nutraceuticals and/or bioceuticals. Example drug product packaging systems including management techniques for fulfilling packaging orders are described in U.S. Pat. Nos. 8,016,095, 8,972,047, 9,299,210, U.S. Patent Publication No. 2020/0407161, and U.S. Design Patent No. 901566 the disclosures of which are hereby incorporated herein by reference.

Pharmacies, including central fill or mail order pharmacies, or other medical facilities responsible for dispensing drug products into packages to fill patient or customer prescriptions may be responsible for complying with laws and regulations governing the handling of certain types of drug products, such as controlled substances, opiates, narcotics, and the like. Some embodiments of the present inventive concept stem from a realization that such restricted access drug products may not be stored in a drug product packaging system when the drug product packaging system is not in use unless the drug product packaging system has a locking mechanism to restrict access to the cells containing the restricted access drug products. Some embodiments of the inventive concept may provide a drug product packaging system that includes a locking mechanism to maintain one or more cells in a locked state in the drug product packaging system. The locking mechanism may allow for insertion of a cell into a cell location protected by the locking mechanism without unlocking other cell locations associated with other cells that have been previously inserted. The controller may be used to provide a user interface identifying the various cell locations in the drug product packaging system and the cells contained therein. A user may select a cell location to unlock, which results in the generation of a control signal in the unlock state, which is communicated to the locking mechanism in the drug product packaging system. In response to the control signal being in the unlock state, an actuator in the locking mechanism operates to unlock a plurality of cell locations protected by the locking mechanism allowing any of the cannisters in these cell locations to be removed. A user may then use the user interface to lock the cell location that was unlocked, which results in the generation of the control signal in the lock state, which is communicated to the locking mechanism in the drug product packaging system. In response to the control signal being in the lock state, the actuator operates to lock the plurality of cell locations protected by the locking mechanism preventing removal of any of the cannisters in these cell locations. If the user fails to lock a cell location that has been unlocked within a defined time threshold, which may be adjustable by the user, the controller may automatically generate the control signal in the lock state to ensure that the restricted access drug products are not left in an accessible state inadvertently. For enhanced security, the controller may maintain a log of the identities of users that have unlocked restricted access cell locations in the drug product packaging system to facilitate tracing of personnel who have had access to the restricted access drug products during, for example, inventory audits of the restricted access drug products.

Referring to FIG. 1, a communication network 100, in accordance with some embodiments of the present inventive concept, comprises a pharmacy management system (PMS) or host system 110, a packaging system management server 120, and multiple drug product packaging systems 130a and 130b that are coupled via a network 140 as shown. The network 140 may be a global network, such as the Internet or other publicly accessible network. Various elements of the network may be interconnected by a wide area network, a local area network, an Intranet, and/or other private network, which may not be accessible by the general public. Thus, the network 140 may represent a combination of public and private networks or a virtual private network (VPN).

The host system 110 may be configured to manage and fill prescriptions for customers. As used herein, PMS or host systems may be used in pharmacies or may be used generally as batch-generating systems for other applications, such as dispensing nutraceuticals or bioceuticals. The host system 110 may be associated with a variety of types of facilities, such as pharmacies, hospitals, long term care facilities, and the like. The PMS system or host system 110 may be any system capable of sending a valid prescription to the one or more product packaging systems 130a and 130b. The packaging system management server 120 may include a cell security module 125 and may be configured to manage the operation of the drug product packaging systems 130a and 130b, which include locations for receiving cells containing drug products therein, respectively. For example, the packaging system management server 120 may be configured to receive packaging orders from the PMS system 110 and to identify which of the drug product packaging systems 130a and 130b should be used to package individual orders or batches of orders. In addition, the packaging system management server 120 may be configured to manage the operations of the drug product packaging systems 130a and 130b. For example, the packaging system management server 120 may be configured to manage the inventory of drug product available through each of the drug product packaging systems 130a and 130b, to manage the drug product dispensing cells assigned or registered to one or more of the drug product packaging systems 130a and 130b, to manage the operational status generally of the drug product packaging systems 130a and 130b, and/or to manage reports regarding the status (e.g., assignment, completion, etc.) of packaging orders, drug product inventory, order billing, and the like. A user 150, such as a pharmacist or pharmacy technician, may communicate with the packaging system management server 120 using any suitable computing device via a wired and/or wireless connection. Although the user 150 is shown communicating with the packaging system management server 120 via a direct connection in FIG. 1, it will be understood that the user 150 may communicate with the packaging system management server 120 via one or more network connections. The user 150 may interact with the packaging system management server 120 to approve or override various recommendations made by the packaging system management server 120 in operating the drug product packaging systems 130a and 130b. The user 150 may also initiate the running of various reports as described above for the drug product packaging systems 130a and 130b. Although only two drug product packaging systems 130a and 130b are shown in FIG. 1, it will be understood that more than two drug product packaging systems may be managed by the packaging system management server 120.

The packaging system management server 120 uses a database management system to manage a database 145 that contains records corresponding to drug product packaging systems 130a and 130b. The packaging system management server further includes the aforementioned cell security module 125 to facilitate management of one or more cell locking mechanisms in the drug product packaging systems 130a and 130b. It will be appreciated that in accordance with various embodiments of the inventive concept, the packaging system management server 120 may be implemented as a single server, separate servers, or a network of servers either co-located in a server farm, for example, or located in different geographic regions.

Although FIG. 1 illustrates an example communication network for controlling access to drug product cells in a drug product packaging system, it will be understood that embodiments of the inventive subject matter are not limited to such configurations, but are intended to encompass any configuration capable of carrying out the operations described herein.

Figure 2:
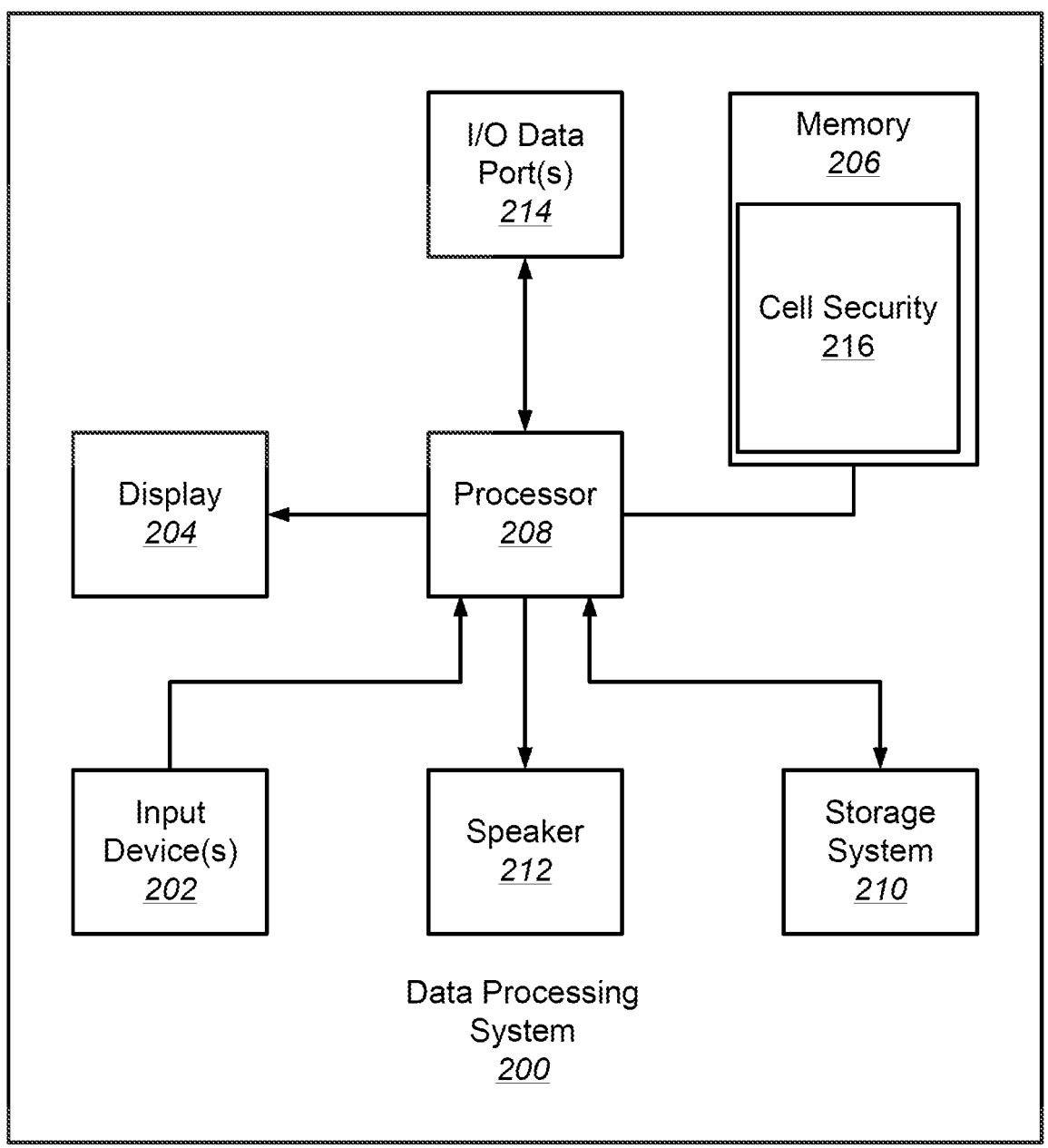
FIG. 2 illustrates a data processing system that may be used to implement the packaging system management server of FIG. 1 in accordance with some embodiments of the inventive concept.

Referring now to FIG. 2, a data processing system 200 that may be used to implement the packaging system management server 120 of FIG. 1, in accordance with some embodiments of the inventive concept, comprises input device(s) 202, such as a keyboard or keypad, a display 204, and a memory 206 that communicate with a processor 208. The data processing system 200 may further include a storage system 210, a speaker 212, and an input/output (I/O) data port(s) 214 that also communicate with the processor 208. The storage system 210 may include removable and/or fixed media, such as floppy disks, ZIP drives, hard disks, or the like, as well as virtual storage, such as a RAMDISK. The I/O data port(s) 214 may be used to transfer information between the data processing system 200 and another computer system or a network (e.g., the Internet). These components may be conventional components, such as those used in many conventional computing devices, and their functionality, with respect to conventional operations, is generally known to those skilled in the art. The memory 206 may be configured with a cell security module 216 to facilitate management of one or more cell locking mechanisms in one or more drug product packaging systems to control access, for example, to cells containing restricted access drug products in accordance with some embodiments of the inventive concept.

Figure 3:
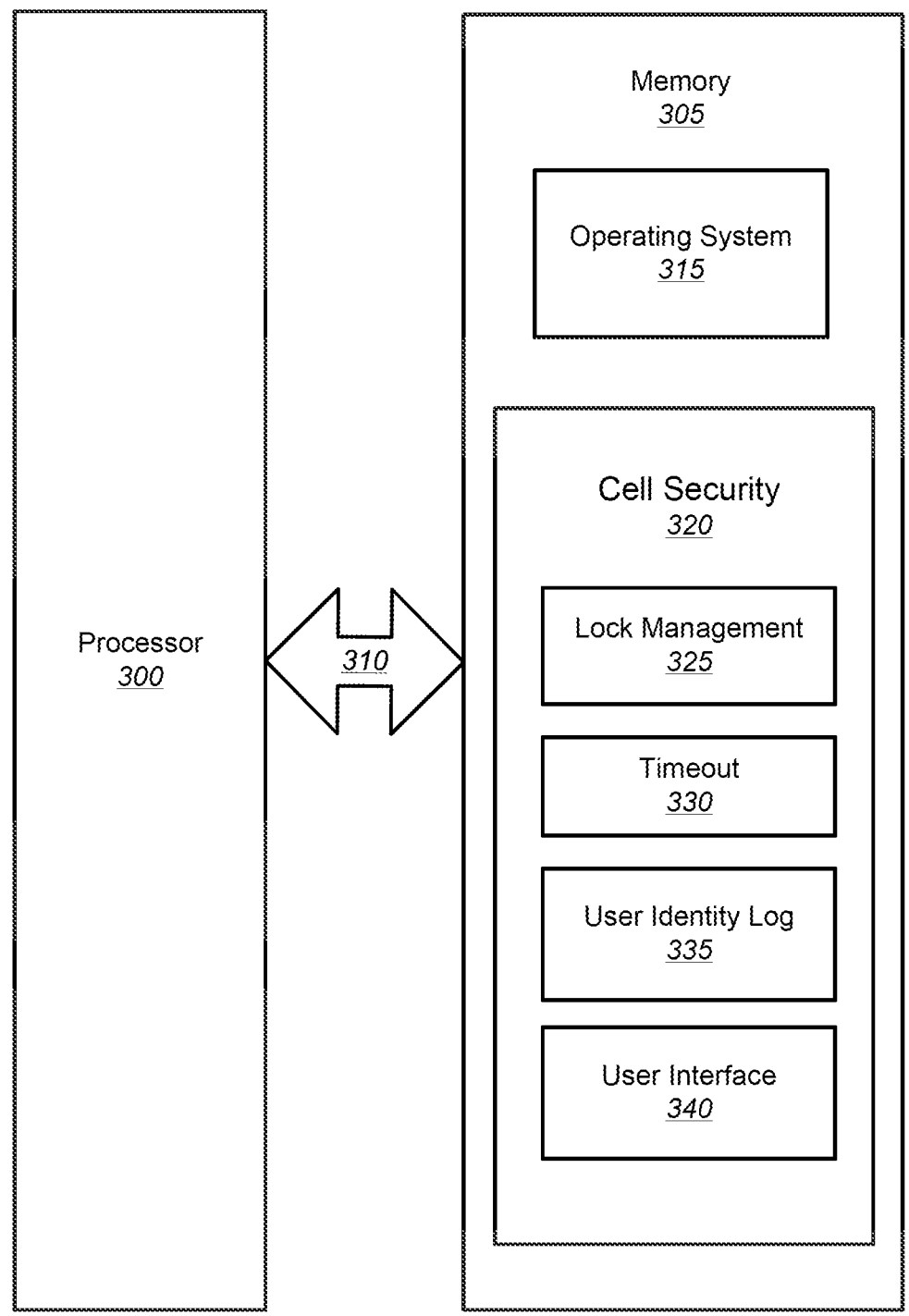
FIG. 3 is a block diagram that illustrates a software/hardware architecture for use in a packaging system management server for controlling access to drug product cells in a drug product packaging system in accordance with some embodiments of the inventive concept.
Figure 5:
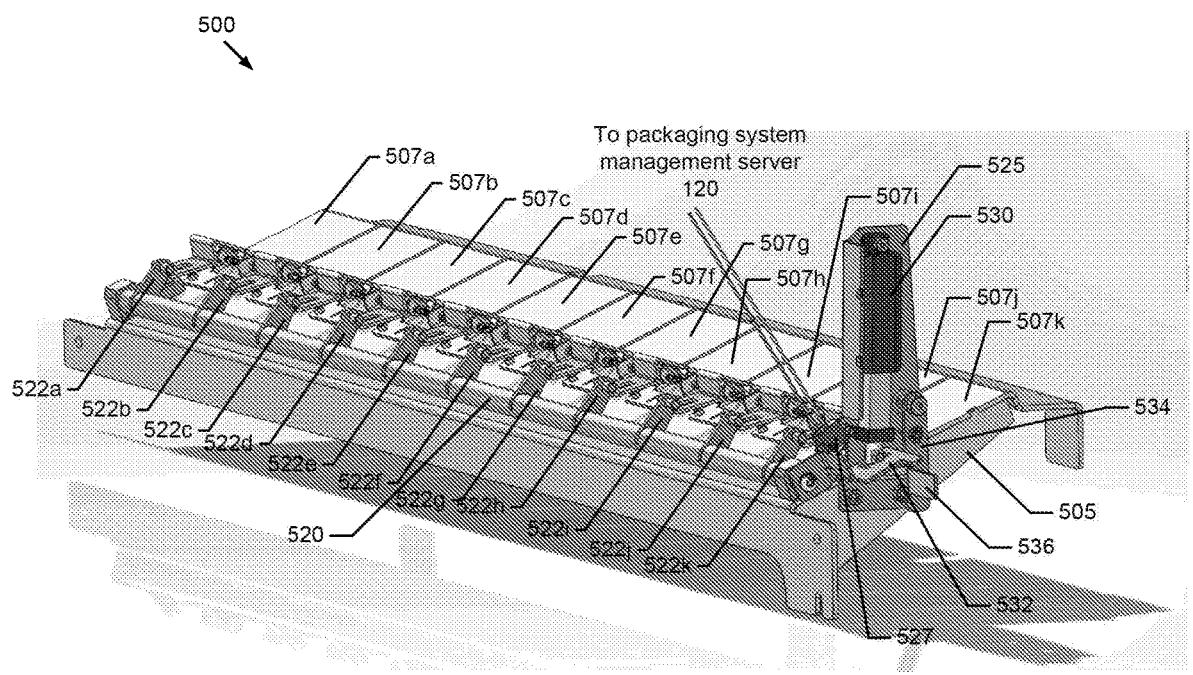
FIGS. 5-11 are perspective views of a locking mechanism used in a drug product packaging system for controlling access to drug product cells in accordance with some embodiments of the inventive concept.

FIG. 3 illustrates a processor 300 and memory 305 that may be used in embodiments of data processing systems, such as the packaging system management server 120 of FIG. 1 and the data processing system 200 of FIG. 2, respectively, for controlling access to drug product cells in a drug product packaging system in accordance with some embodiments of the inventive concept. The processor 300 communicates with the memory 305 via an address/data bus 310. The processor 300 may be, for example, a commercially available or custom microprocessor. The memory 305 is representative of the one or more memory devices containing the software and data used for controlling access to drug product cells in a drug product packaging system in accordance with some embodiments of the inventive concept. The memory 305 may include, but is not limited to, the following types of devices: cache, ROM, PROM, EPROM, EEPROM, flash, SRAM, and DRAM.

As shown in FIG. 3, the memory 305 may contain two or more categories of software and/or data: an operating system 315 and a cell security module 320. In particular, the operating system 315 may manage the data processing system's software and/or hardware resources and may coordinate execution of programs by the processor 300. The cell security module 320 may comprise a lock management module 325, a timeout module 330, a user identity log module 335, and a user interface module 340. The lock management module 325 may be configured to generate a control signal in a lock state or an unlock state in response, for example, to user input received through the user interface module 340, and to communicate the control signal to a locking mechanism included in a drug product packaging system. The locking mechanism may be configured to unlock one or more cell locations in response to receiving the control signal in the unlock state and to lock the one or more cell locations in response to receiving the control signal in the lock state.

The timeout module 330 may be configured to manage a timer that starts once the lock management module 325 generates the control signal in the unlock state. If user input has not been received by way of the user interface 340 triggering generation of the control signal in the lock state by the expiration of a time threshold, then the timeout module 330 may generate the control signal in the lock state to cause the locking mechanism to lock the one or more cell locations for which it is responsible to ensure that restricted access drug products are not inadvertently left unsecured. In some embodiments, the time threshold may be about two minutes.

The user identity log module 335 may be configured to maintain a log of the identities of users that have accessed the user interface 340 to unlock restricted access cells in the drug product packaging system to facilitate tracing of personnel who have had access to the restricted access drug products contained in those cells. This information may be useful for tracing personnel access to restricted access drug products during inventory audits or other investigations.

The user interface module 340 may be configured to display a status of the cells in a drug product packaging system. This is illustrated, for example, in FIG. 4 in which the user interface module 340 displays the drug product name, drug product code, cell capacity, and cell address for nine drug products A through I in accordance with an example embodiment of the inventive concept. As shown in FIG. 4, drug products A, F, and H are in a lockable row F in cell positions 4, 8, and 1, respectively. Drug products B-E, G, and I are in cell locations that are not protected by a locking mechanism. A user may provide input via the user interface 340 to lock or unlock the cell containing drug product A, F, or H, which will trigger a control signal generated by the lock management module 325 to cause the locking mechanism to carry out the requested operation for the particular cell location for which user input was received.

Although FIG. 3 illustrates hardware/software architectures that may be used in data processing systems, such as the packaging system management server 120 of FIG. 1 and the data processing system 200 of FIG. 2, respectively, for controlling access to drug product cells in a drug product packaging system in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-3 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the packaging system management server 120 of FIG. 1, the data processing system 200 of FIG. 2, and the hardware/software architecture of FIG. 3 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus of FIGS. 1-4 may be used for controlling access to drug product cells in a drug product packaging system according to various embodiments described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 206 coupled to the processor 208 and the memory 305 coupled to the processor 300 include computer readable program code that, when executed by the respective processors, causes the respective processors to perform operations including one or more of the operations described herein.

Figure 10:
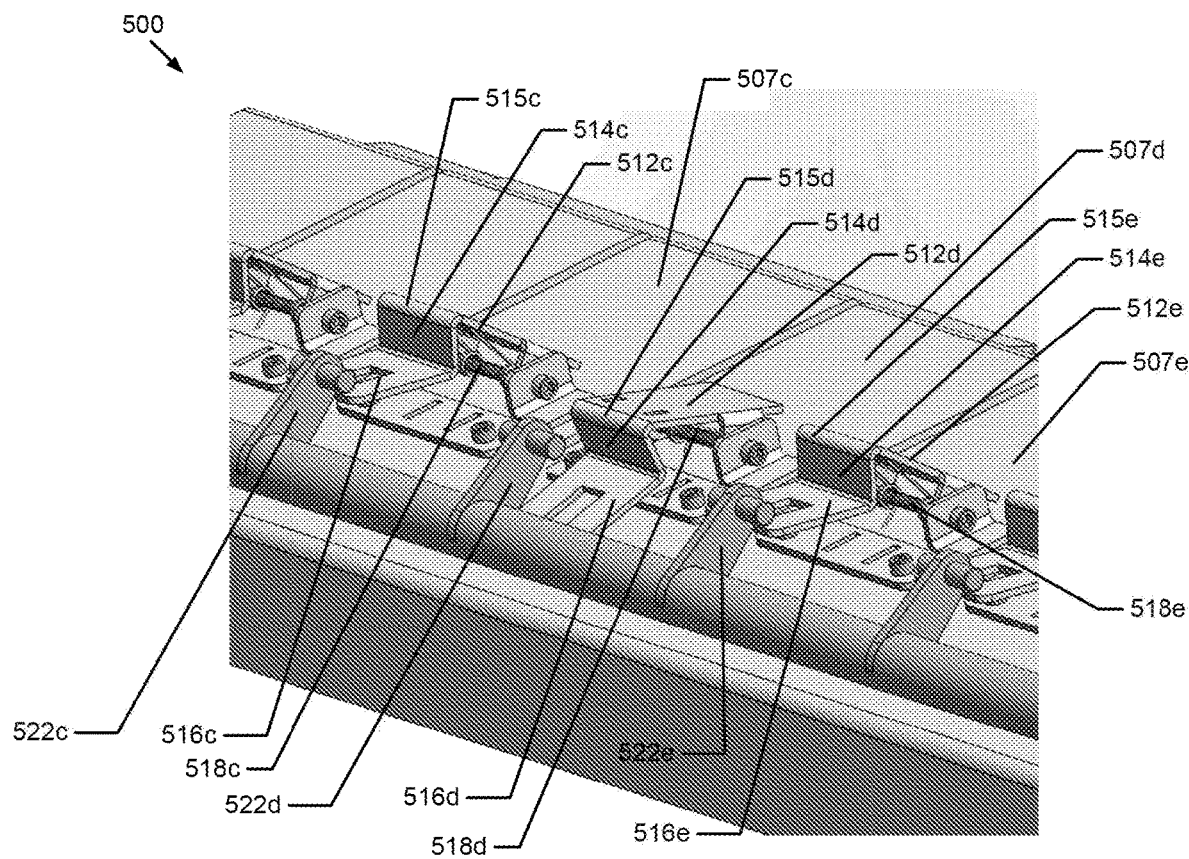
Figure 11:
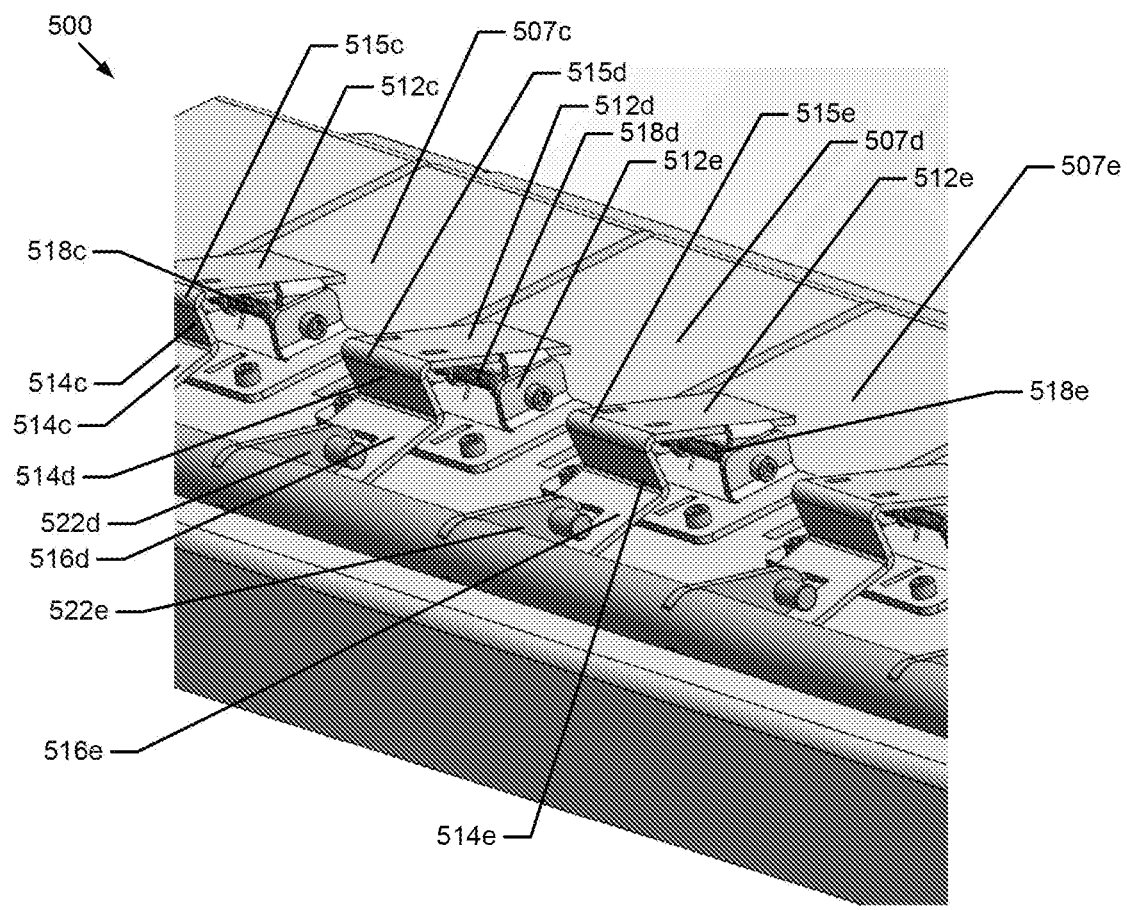
Figure 12:
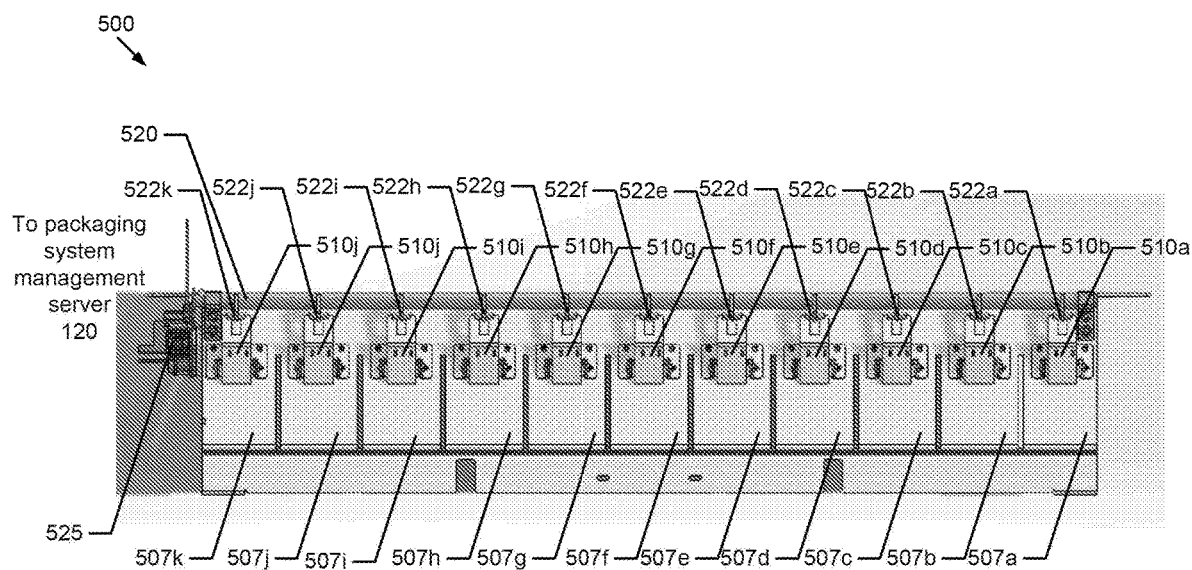
FIG. 12 is a plan view of the locking system used in a drug product packaging system for controlling access to drug product cells in accordance with some embodiments of the inventive concept.

FIGS. 5-11 are perspective views of a locking mechanism used in a drug product packaging system for controlling access to drug product cells in accordance with some embodiments of the inventive concept. FIG. 12 is a plan view of the locking system used in a drug product packaging system for controlling access to drug product cells in accordance with some embodiments of the inventive concept. Referring now to FIGS. 5-10, the locking mechanism 500 for a drug product packaging system may include a base portion 505 that defines a plurality of slots for receiving a plurality of cells, respectively, for holding drug products along a row. The base portion 505 may be installed as a row or partial row in a drug product packaging system, such as the drug product packaging systems 130a and 130b of FIG. 1. In the example of FIGS. 5-10, eleven slots 507a-507k are defined with each slot including latch 510a-510k, respectively. Each latch 510a-510k includes a sloped receiving portion 512a-512k, a wall portion 514a-514k that is coupled to the sloped receiving portion 512a-512k at a junction 515a-515k, and a tab portion 516a-516k that is coupled to the wall portion. The plurality of latches 510a-510k rest upon a plurality springs 518a-518k, respectively, which may be implemented as torsion-type springs or compression-type springs. The locking mechanism 500 further comprises a rod 520 that includes a plurality of members 522a-522k extending therefrom that respectively correspond to the plurality of latches 510a-510k. As will be described herein, the rod 520 is configured to rotate between positions to allow the members 522a-522k to engage the tab portions 516a-516k of the latches 510a-510k. An actuator 525 is coupled to the base 505 and includes a communication interface component 527 to receive a control signal from the packaging system management server 120 via the lock management module 325 and/or the timeout module 330. The actuator 525 includes a piston 530 that is configured to extend or retract responsive to the control signal received via the communication interface component 527. The piston 530 is configured to engage a lever 532 that is coupled to the rod 520 to rotate the rod 520 between positions responsive to piston 530 moving between an extended or retracted position. The actuator 525 may further include a latch 534 that is positioned proximate to the lever 532 configured to rotate about an axis to mechanically hold the lever 532 in a position corresponding to the piston 530 being in the extended position.

Figure 6:
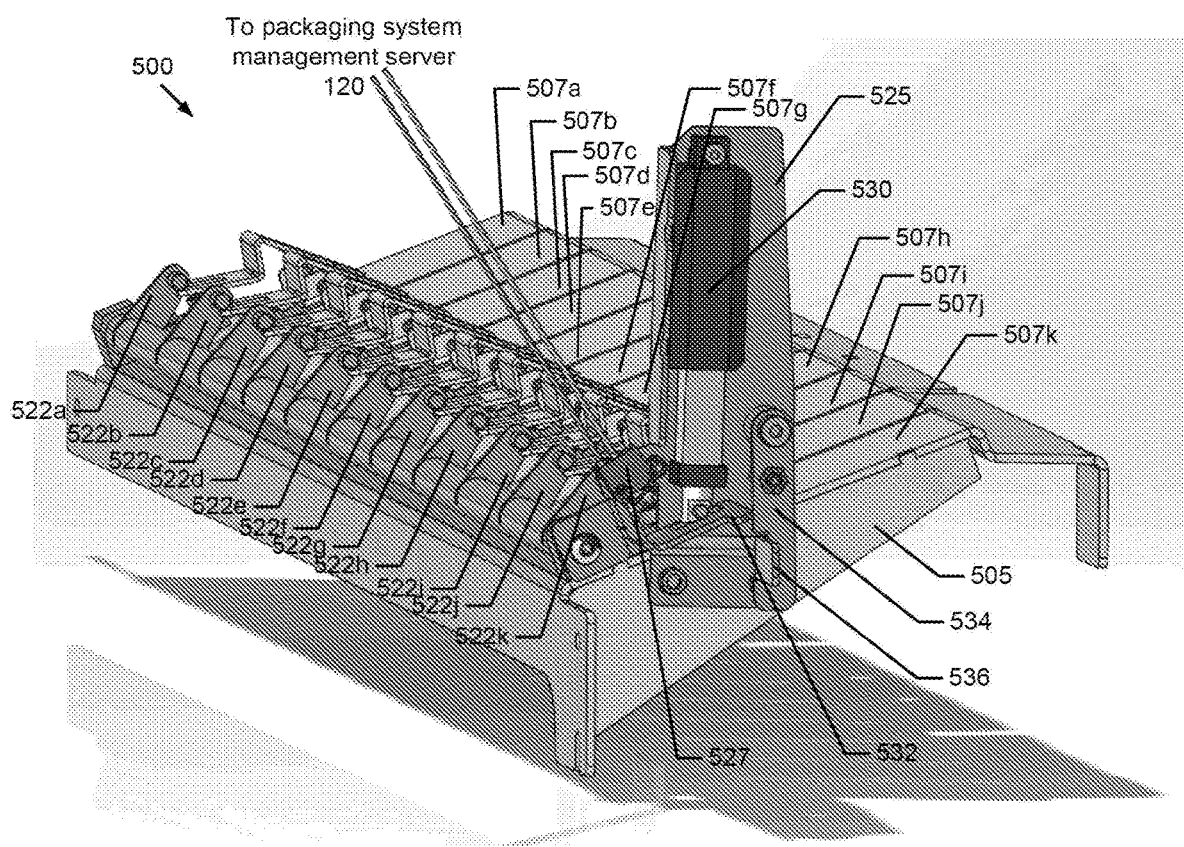
Figure 7:
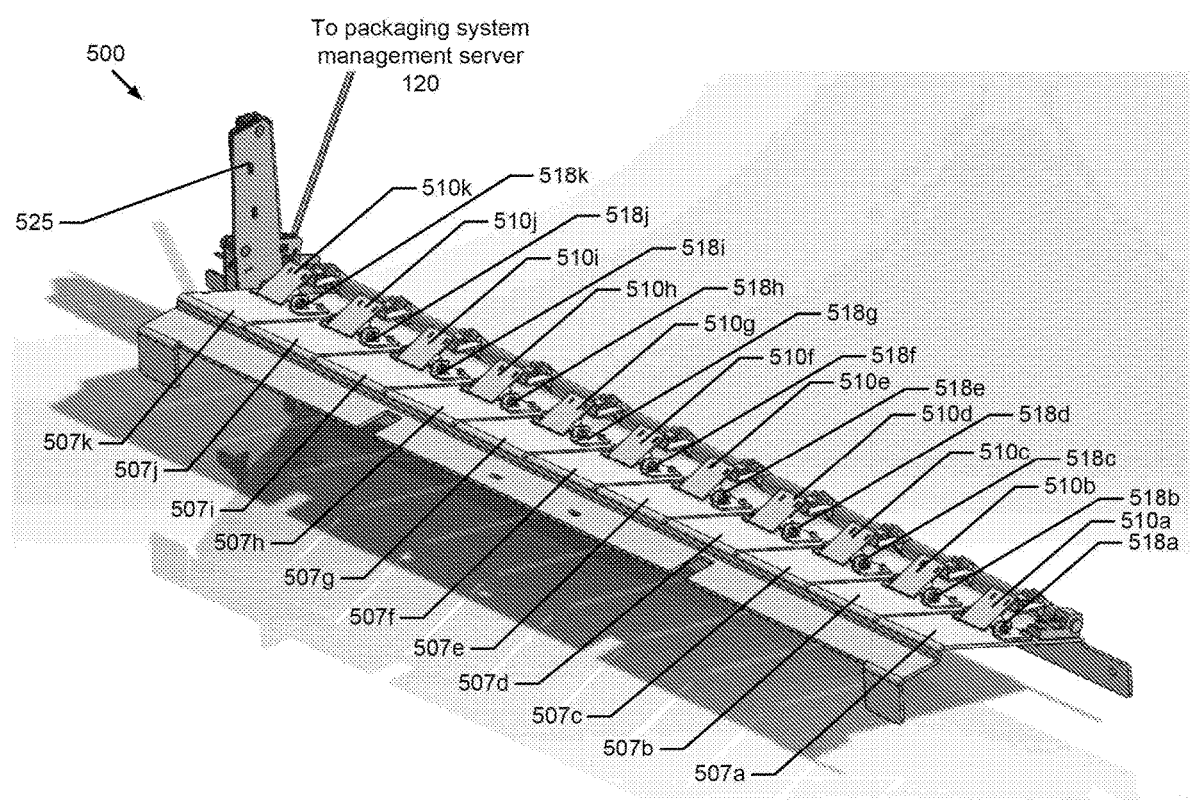
Figure 8:
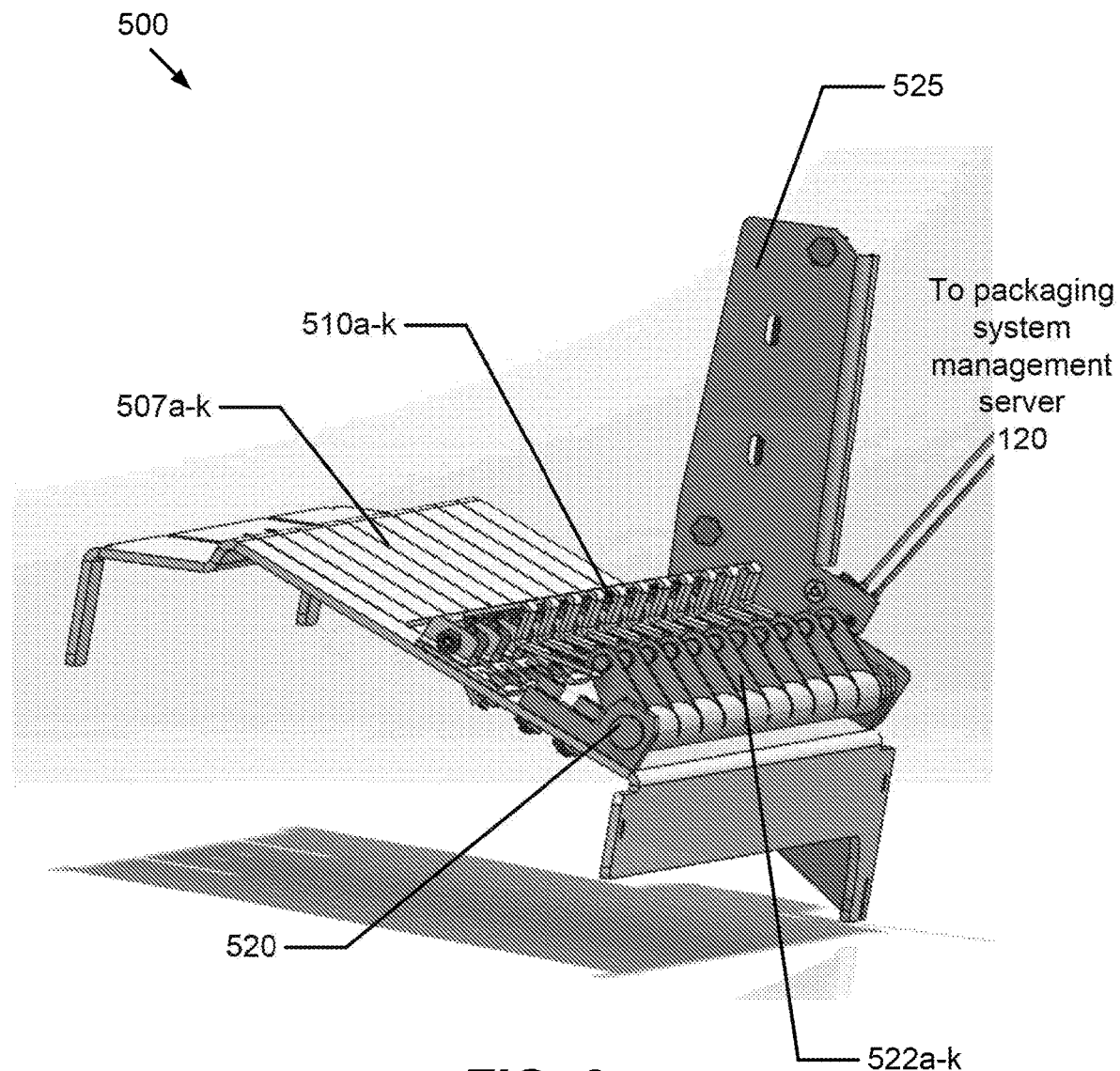
Figure 9:
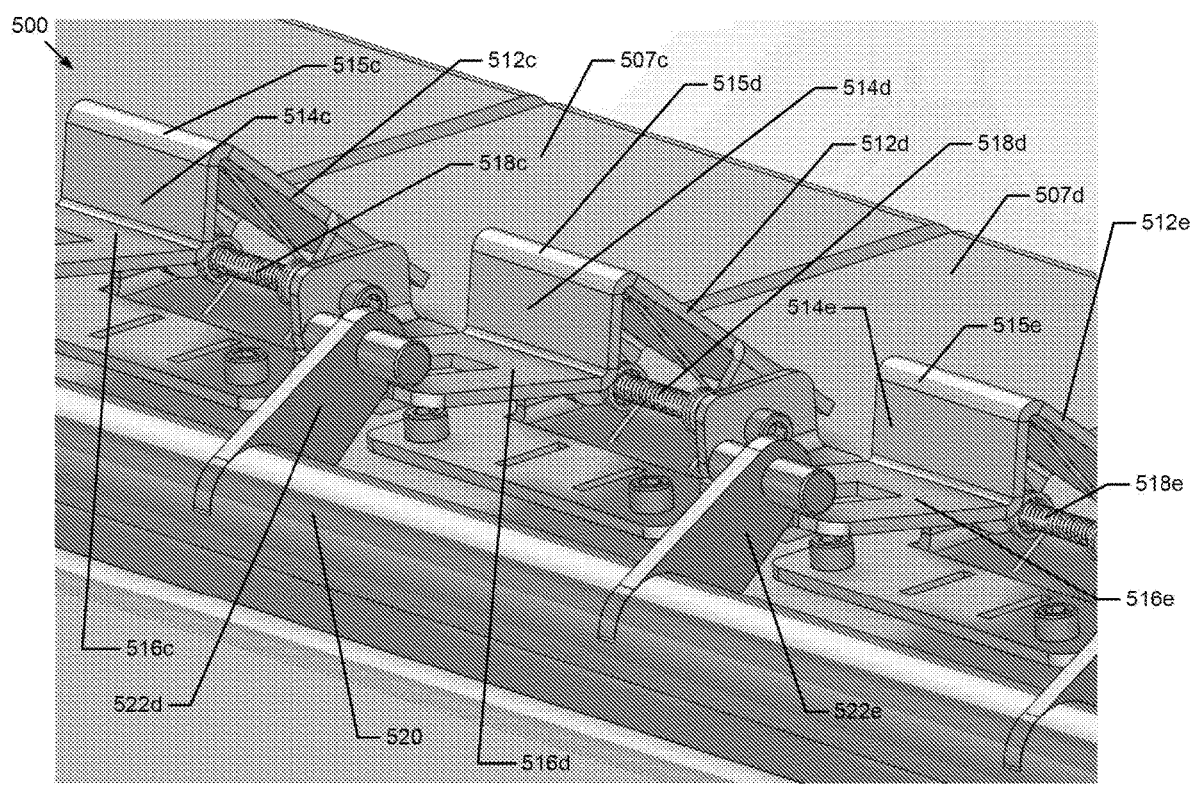

Example operations of the locking mechanism 500 for receiving a cell, according to some embodiments of the inventive concept, will now be described with reference to FIGS. 6, 9, and 10. Referring to FIGS. 9-10, a cell containing a drug product may be received in slot 507d. The cell may be pushed against the sloped receiving portion 512d of the latch 510d thereby causing the latch 510d to compress the spring 518d as shown in FIG. 10. The cell is pushed farther into the slot 507d further compressing the spring 518d until a lip or flange on a bottom surface of the cell moves past the junction 515d, which results in the spring 518d returning to an extended position to push the junction 515d into a bottom surface of the cell. The overlap between the wall 514d and the lip or flange on the cell inhibits or prevents removal of the cell from the location slot 507d without causing damage to the cell.

Example operations for locking and unlocking the locations protected by the locking mechanism 500, according to some embodiments of the inventive concept, will now be described with respect to FIGS. 6, 9, and 11. In response to a control signal generated by the packaging system management server 120 via the lock management module 325 and/or the timeout module 330, the actuator 525 moves the piston between a retracted and an extended position. When the control signal is generated in an unlock state, the actuator 525 causes the piston to 530 to extend. The extension of the piston 530 results in downward force on the lever 532, which rotates the rod 520 into a first position in which the members 522a-522k engage the tab portions 516a-516k to cause the latches 510a-510k to compress the springs 518a-518k as shown in FIG. 11. The latches 510a-510k are configured in the unlock position with the springs 518a-518k compressed allowing any of the cells in the locations corresponding to slots 507a-507k to be removed as there is no overlap between a lip or flange on the cell and the walls 514a-514k. When the control signal is generated in the lock state as a result of user input or operation of the timeout module 330, the actuator 525 causes the piston 530 to retract. The retraction of the piston 530 allows the energy stored in the springs 518a-518k to exert upward force on the latches 510a-510k moving the latches 510a-510k into the lock position in which the walls 514a-514k overlap with the lip or flange on any cell remaining in the locations corresponding to slots 507a-507k. The upward movement of the latches 510a-510k causes the tab portions 516a-516k to exert force on the members 522a-522k to rotate the rod 520 to a second position associated with the locked position of the latches 510a-510k.

To ensure that restricted access cells can be accessed should there be a loss of power or a communication failure between the packaging system management server 120 and the locking mechanism 500, the appropriate housing on the drug product packaging system 130a or 130b may be removed to allow access to the lever 532 and the latch 534. This may allow the lever 532 to be manually manipulated. Accordingly, a technician may depress the lever 532 rotating the rod 520 into the first position resulting in the latches 510a-510k assuming the unlock position in which the springs 518a-518k are compressed. The technician may rotate the latch 534 so that the tab 536 extending from the latch 534 is placed over the lever 532 holding the compression on the springs 518a-518k and preventing the latches 510a-510k from returning to the lock state. This may allow the technician to remove any needed cells containing restricted access drug product. The latch 534 may then be rotated away from the lever 532 to allow the springs 518a-518k to return to an extended position and allowing the latches 510a-510k to return to the lock state.

Figure 13:
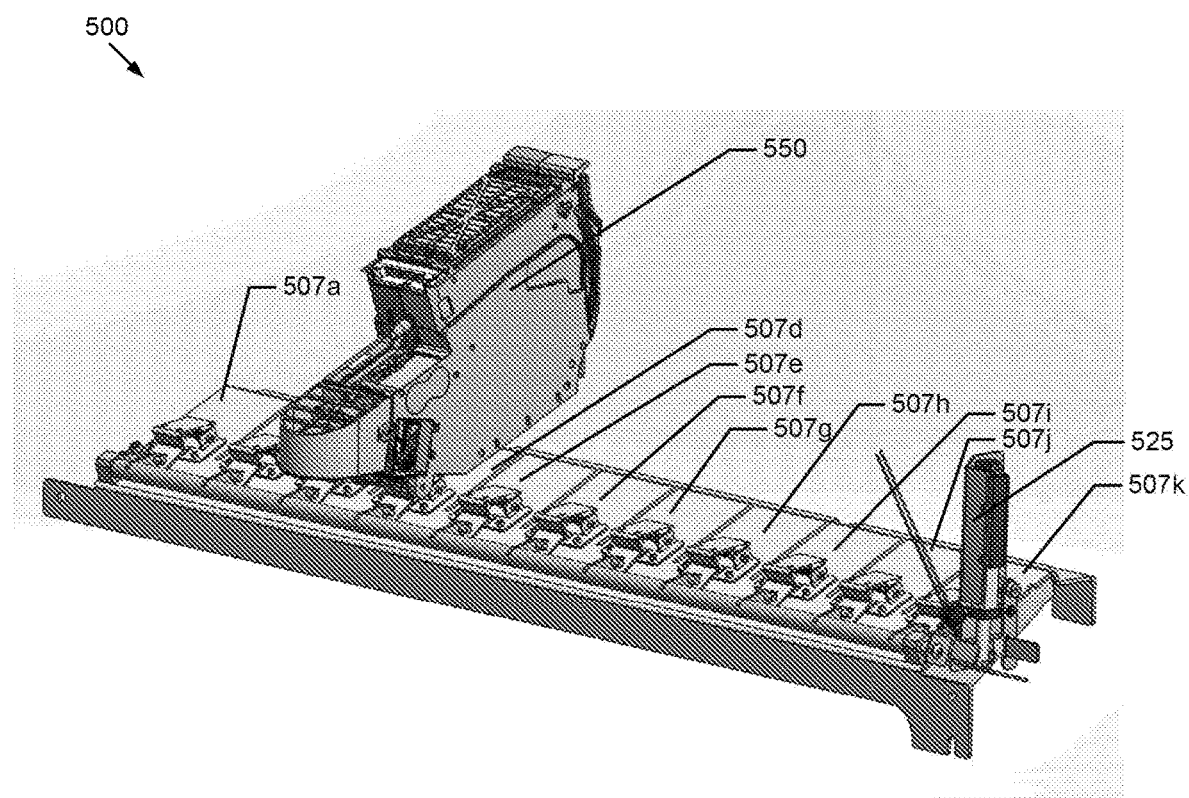
FIG. 13 is a perspective view and FIGS. 14 and 15 are elevation views that illustrate the reception and release of a drug product cell in the locking system used in a drug product packaging system in accordance with some embodiments of the inventive concept.
Figure 14:
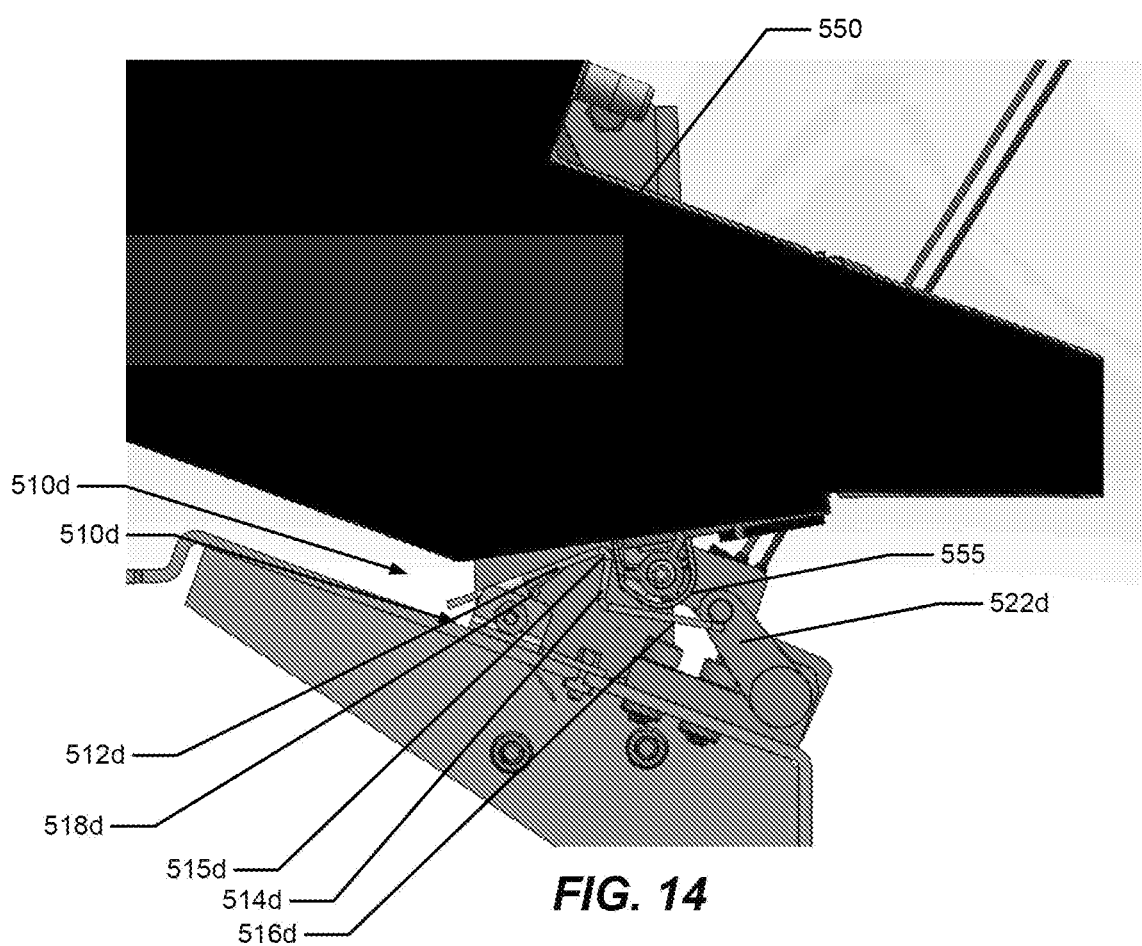
Figure 15:
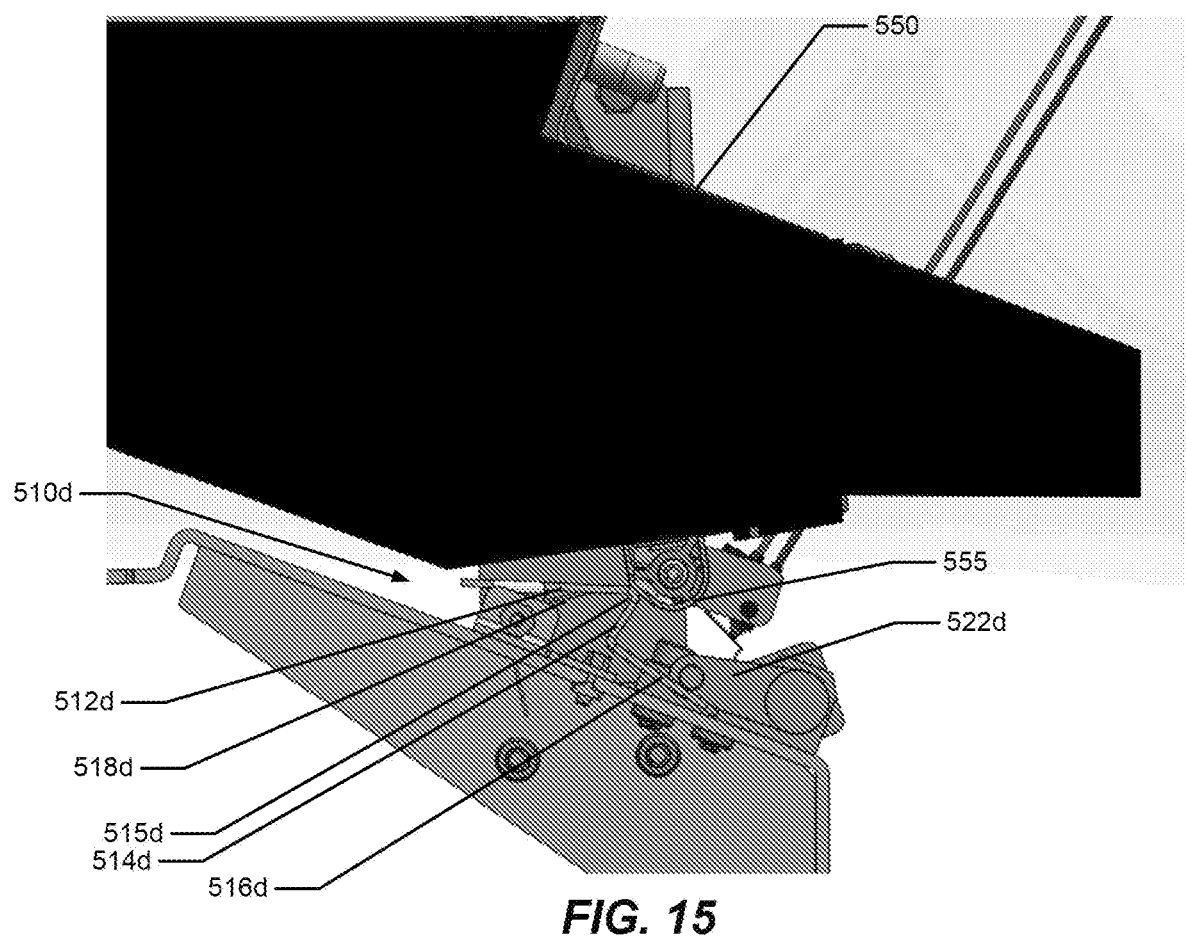

FIG. 13 is a perspective view and FIGS. 14 and 15 are elevation views that illustrate the reception and release of a drug product cell in the locking system used in a drug product packaging system in accordance with some embodiments of the inventive concept. Referring now to FIG. 13, a cell 550 is shown locked into place in slot 507d of the locking mechanism 500. FIG. 14 is an elevation view that illustrates the latch 510*d* in the lock position and engaged with the cell 550. As shown in FIG. 14, the spring 518*d* is in the extended position such that the lip or flange 555 of the cell 550 overlaps with the wall 514*d* of the latch 510*d* to hold the cell 550 securely in the latch. Referring now to FIG. 15 is an elevation view that illustrates the latch 510*d* in the unlock position. As shown in FIG. 15, the spring 518*d* is in the compressed position allowing the lip or flange 555 of the cell 550 to be pulled over the junction 515*d* to be free from overlap with the wall 514*d* so that the cell 550 can be removed from the slot 507*d*.

Embodiments of the inventive concept may provide a drug product packaging system including a locking mechanism 500 that may allow cells to be inserted into locations protected by the locking mechanism 500 without the need for performing an unlock operation on the destination location or unlocking other locations protected by the locking mechanism 500. The locking mechanism 500 may include an actuator 525 that may be operable responsive to a control signal from the packaging system management server 120 generated in an unlock state to unlock all locations protected by the locking mechanism 500 for removal of one or more cells from the unlocked locations. The actuator 525 may be further operable responsive to the control signal being generated in the lock state to lock the locations thereby inhibiting or preventing removal of cells therefrom. A user interface may be provided to select locations to be unlocked or locked resulting in the generation of the appropriate control signal from the packaging system management server 120. The locking mechanism 500 may allow restricted access drug products, which may be required to be stored in a secure storage unit, such as a safe, when not in use, to remain in the drug product packaging system 130*a*, 130*b* in compliance with any governing laws or regulations. As a result, technicians need not empty a drug product packaging system 130*a*, 130*b* of all restricted access drug products for storage in a safe or other secure storage unit during non-business hours.

Further Definitions and Embodiments:

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and/or block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises," "comprising," "include", "including", "includes", "have", "has", "having", or variants thereof when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

It will also be understood that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The description of the present disclosure has been presented for purposes of illustration, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described to best explain the principles of the disclosure and the practical application, and to enable others of ordinary skill in the art to understand the disclosure with various modifications as are suited to the particular use contemplated.

What is claimed is:

1. A system, comprising:
   a drug product packaging system that is configured to hold a plurality of cells in a lockable section thereof and to maintain the plurality of cells in a locked state via a locking system, the locking system being configured to receive ones of the plurality of cells into the lockable section of the drug product packaging system and configured to maintain the ones of the plurality of cells in the locked state without changing the locked state of previously received ones of the plurality of cells into the lockable section of the drug product packaging system; and
   a controller that is configured to generate a control signal in a lock state or an unlock state;
   wherein the locking system comprises:
      a plurality of latches, each of the plurality of latches being configured to receive a respective one of the plurality of cells, each of the plurality of latches being configurable between a lock position to maintain the respective one of the plurality of cells in the locked state and an unlock position to maintain the respective one of the plurality of cells in the unlocked state; and
      a latch engagement apparatus that is configured to mechanically engage the plurality of latches to configure the plurality of latches in the lock position and to configure the plurality of latches in the unlock position responsive to force applied thereto.

2. The system of claim 1, wherein the drug product packaging system is configured to transition the plurality of cells to the locked state when the plurality of cells have been in an unlocked state for a time threshold.

3. The system of claim 2, wherein each of the plurality of latches comprises:
   a sloped receiving portion;
   a wall coupled to the sloped receiving portion at a junction; and
   a tab coupled to the wall.

4. The system of claim 3, wherein the wall of each respective one of the plurality of latches is configured to block removal of the respective one of the plurality of cells when the respective one of the plurality of latches is in the lock position; and
   wherein the wall of each respective one of the plurality of latches is configured to facilitate removal of the respective one of the plurality of cells when the respective one of the plurality of latches is in the unlock position.

5. The system of claim 3, wherein the locking system further comprises:
   a plurality of springs respectively associated with the plurality of latches, respective ones of the plurality of springs being in a compressed state when respective ones of the plurality of latches are in the unlock position and being in an extended state when respective ones of the plurality of latches are in the lock position.

6. The system of claim 5, wherein the plurality of springs are configured to engage the sloped receiving portions of the plurality of latches, respectively.

7. The system of claim 5, wherein each of the plurality of springs is a torsion-type spring or a compression-type spring.

8. The system of claim 5, wherein the latch engagement apparatus further comprises:
a rod comprising a plurality of members extending therefrom, the plurality of members corresponding to the plurality of latches, respectively; and
wherein the locking system further comprises:
an actuator that is coupled to the rod and is configured to rotate the rod between a first position in which the plurality of members of the rod engage the plurality of tabs of the plurality of latches to configure the plurality of latches in the unlock position and to configure the plurality of springs in the compressed state and a second position to configure the plurality of latches in the lock position and the plurality of springs in the extended state.

9. The system of claim 8, wherein the latch engagement apparatus further comprises:
a lever coupled to the rod that is configured to rotate the rod between the first position in which the plurality of members of the rod engage the plurality of tabs of the plurality of latches to configure the plurality of latches in the unlock position and to configure the plurality of springs in the compressed state and the second position to configure the plurality of latches in the lock position and the plurality of springs in the extended state responsive to the force applied thereto.

10. The system of claim 8, wherein the actuator is configured to rotate the rod to the first position responsive to the control signal being generated in the unlock state and is configured to rotate the rod to the second position responsive to the control signal being generated in the lock state.

11. The system of claim 10, wherein the controller is configured to generate the control signal in the lock state when the rod has been in the first position for the time threshold.

12. The system of claim 11, wherein the time threshold is about two minutes.

13. The system of claim 10, wherein the controller is configured to generate the control signal responsive to user input.

14. The system of claim 13, wherein the controller is configured to record an identification of a user that provides the user input.

15. The system of claim 8, wherein the actuator is a piston type actuator.

16. The system of claim 8, further comprising:
a latch that is configured to hold the rod in the first position in which the plurality of members engage the plurality of tabs of the plurality of latches to configure the plurality of latches in the unlock position and to configure the plurality of springs in the compressed state.

17. A method, comprising:
receiving, using a locking system, a first cell into a lockable section of a drug product packaging system configured to hold a plurality of cells in the lockable section thereof, the locking system comprising a plurality of latches, each of the plurality of latches being configured to receive a respective one of the plurality of cells, each of the plurality of latches being configurable between a lock position to maintain the respective one of the plurality of cells in a locked state and an unlock position to maintain the respective one of the plurality of cells in an unlocked state;
maintaining, using the locking system, the first cell in the locked state;
receiving, using the locking system, a second cell into the lockable section of the drug product packaging system without changing the locked state of the first cell;
generating a control signal in a lock state or an unlock state; and
mechanically engaging the plurality of latches using a latch engagement apparatus to configure the plurality of latches in the lock position and to configure the plurality of latches in the unlock position responsive to force applied thereto.

18. The method of claim 17, further comprising:
operating the locking system to unlock the lockable section of the drug product packaging system responsive to the control signal being in the unlock state such that the first cell and the second cell are maintained in the unlocked state; and
operating the locking system to lock the lockable section of the drug product packaging system responsive to the control signal being in the lock state such that the first cell and the second cell are maintained in the locked state.

19. The method of claim 17, wherein generating the control signal comprises generating the control signal responsive to user input.

20. The method of claim 19, further comprising:
recording an identification of a user that provides the user input.

* * * * *